United States Patent [19]

Spibey

[11] Patent Number: 5,616,326
[45] Date of Patent: Apr. 1, 1997

[54] RECOMBINANT CANINE ADENOVIRUS 2 (CAV-2)

[75] Inventor: Norman Spibey, Glasgow, Scotland

[73] Assignee: The University Court of the University of Glasgow, Glasgow, Scotland

[21] Appl. No.: 247,296

[22] Filed: May 23, 1994

Related U.S. Application Data

[63] Continuation of Ser. No. 915,688, filed as PCT/GB91/00107 Jan. 25, 1991 published as WO91/11525 Aug. 8, 1991, abandoned.

[30] Foreign Application Priority Data

Jan. 25, 1990 [GB] United Kingdom .................... 900176

[51] Int. Cl.$^6$ .................... A61K 39/235; A61K 39/205; A61K 39/21; C12N 7/01; C12N 15/47; C12N 15/48; C12N 15/49
[52] U.S. Cl. .................... 424/199.1; 424/205.1; 424/233.1; 424/818; 424/819; 424/224.1; 424/207.1; 424/208.1; 435/235.1; 435/252.3; 435/320.1
[58] Field of Search .................... 424/205.1, 233.1, 424/199.1, 818, 819, 224.1, 207.1, 208.1; 435/320.1, 252.3, 235.1

[56] References Cited

U.S. PATENT DOCUMENTS 4,920,209  4/1990  Davis et al. .

FOREIGN PATENT DOCUMENTS 0181117  5/1986  European Pat. Off. .

OTHER PUBLICATIONS

N. Spibey, et al; Identification and nucleotide sequence of the early region 1 from canine adenovirus types 1 and 2; *Virus Research* 14, pp. 241–256 (1989).

M. Shinagawa, et al; *Phylogenetic relationships between adenoviruses as inferred from nucleotide sequences of inverted terminal repeats; Gene* 55 pp. 85–93 (1987).

KC Chow, In Vitro Adenovirus DNA Replication; *Diss Abstr Int (Sci)* 45(10 3223B (1985).

K. Wang and G.D. Pearson; Adenovirus sequences required for replication in vivo; *Nucl. Acids Res.* 13(14) pp. 5173–5187 (1985).

F.L. Graham; Adenoviruses as expression vectors and recombinant vaccines, *Trends in Biotechnology* 8, pp. 85–87 (Apr. 1990).

Primary Examiner—Anthony C. Caputa
Attorney, Agent, or Firm—Bell, Seltzer, Park & Gibson

[57] ABSTRACT

A non-essential region in strains of live non-pathogenic immunogenic canine adenovirus is described. The insertion of genes from pathogenic carnivora viruses into this region, with suitable expression control systems, without prejudicing the stable reproducibility of the adenovirus vector is described. Such recombinant canine adenoviruses modified to contain a gene coding for an antigen or immunogenic agent, in association with an effective promoter for the gene, are described.

9 Claims, 1 Drawing Sheet

Fig. 1

```
  1         10         20         30         40         50         60
CATCATCAAT AATATACAGG ACAAAGAGGT GTGGCTTAAA TTTGGGCCGTT GCAAGGGGCG 70         80         90        100        110        120
GGGTCATGGG ACGGTCAGGT TCAGGTCACG CCCTGGTCAG GGTGTTCCCA CGGGAATGTC 130        140        150        160        170        180
CAGTGACGTC AAAGGGCGTGG TTTTACGACA GGGCGAGTTC CGCGGACTTT TGGCCGGCGC 190        200        210        220        230        240
CCGGGTTTTT GGGCGTTGTG CCTATTTGTG GTTTTGTGGT TGACAGGGTG ACAAGGACGT 250        260        270        280        290        300
GCTGTACTTT TTGTGAACTT TCCGGGCCAA CCGCCAAAGG GAAACTGCAC TTAACATTTA 310        320        330        340        350        360
CCACGCGCCC ACAATTTATG ACTGTACTTG GCACCACTTC CTCAAACGCC CCGTTATATT 370        380        390        400        410        420
CCTTTTGCTT TTCCACACGC CCTACTTTGA GGACTATATA AACGCTGTGC TTGGCATTTC 430        440        450        460        470        480
ATCCTCATAG CTCTCCCTCTG ACAGCCAGCC GTCCGTGAGT ACTATGGCAG CTTTAGGAGT 490        500        510        520        530        540
GTCTATGGGA GCATGTTTTT GTCTGAGGCT TCACAAGAGT CTAGTGGAGA GTGTGTGTGC 550        560        570        580        590        600
TCAACTGAGA CTTACGAACT TTTTGCCTTC TGAACTCGCC GTGTGGTGTT TAGCCTTATT 610        620        630        640        650
AGGGCCCAGG AAGTGCGTCC GTGTCCTACC TTGCCGCGGC TGTTTCGGTT TA
```

RECOMBINANT CANINE ADENOVIRUS 2 (CAV-2)

This application is a continuation of prior application Ser. No. 07/915,688, filed on Aug. 19, 1992 (now abandoned), the disclosure of which is incorporated by reference herein in its entirety, which is the national phase of PCT/GB91/00107, filed Jan 25, 1991.

FIELD OF THE INVENTION

The present invention relates to vaccines for use in carnivora and in particular to viral vaccines against diseases such as rabies, canine and feline parvovirus, and feline leukaemia virus. These would have distinct advantages over those in current use.

BACKGROUND OF THE INVENTION

Recently there has been proposed a DNA vector system wherein a gene coding for the target antigen is inserted into a live adenovirus which is then formulated in an enteric coated dosage form.

However, many adenoviruses are known. The selection of a suitable virus to act as a vector for the gene, and the identification of a suitable non-essential region as a site for insertion of the gene pose a challenge. In particular, the insertion site must be non-essential for the viable replication of the virus and its effective operation in vivo. Moreover, the insertion site must be capable of accepting a considerable amount of new genetic material, whilst ensuring that the virus continues to replicate. The CAV-2 adenovirus is known to be a safe vector but its DNA comprises some 31,000 base pairs which must be searched to identify a suitable site or indeed to establish whether a suitable site exists or not.

SUMMARY OF THE INVENTION

The present inventors have now identified a suitable non-essential region in strains of live non-pathogenic immunogenic canine CAV-2 type adenovirus and have succeeded in inserting genes from pathogenic carnivora viruses with suitable expression control systems without prejudicing the stable reproducibility of the adenovirus vector.

A first aspect of the present invention provides a recombinant virus for producing antibodies or cell mediated immunity to an infectious organism in carnivora, which comprises a live non-pathogenic immunogenic viable canine adenovirus modified so as to contain a gene coding for the antigen which corresponds to said antibodies or induces said cell mediated immunity, in association with an effective promoter for said gene formed and arranged for expression of said antibodies or cell mediated immunity elements in immunogenic non-pathogenic quantities; the promoter-gene sequence being introduced into a region of the viral genome which extends from the SmaI site close to the end of the inverted terminal repeat (ITR) up to the promoter for the early region 4(E4).

A second aspect of the present invention provides a method of preparing a viable recombinant virus for producing antibodies or cell mediated immunity to an infectious organism in carnivora, which comprises inserting into a live non-pathogenic canine adenovirus the gene coding for the antigen which corresponds to said antibodies or induces said cell mediated immunity.

A third aspect of the invention relates to a plasmid containing such a viral DNA sequence containing a promoter-gene construct.

A fourth aspect of the invention provides a vaccine formulation which comprises the recombinant vaccine in association with an acceptable carrier.

BRIEF DESCRIPTION OF THE DRAWING

FIG. 1 is the DNA sequence of the right hand terminal region of the canine adenovirus type 2 (SEQ ID NO: 1).

DESCRIPTION OF PREFERRED EMBODIMENTS

A first aspect of the present invention provides a recombinant virus for producing antibodies or cell mediated immunity to an infectious organism in carnivora, which comprises a liver non-pathogenic immunogenic viable canine adenovirus modified so as to contain a gene coding for the antigen which corresponds to said antibodies or induces said cell mediated immunity, in association with an effective promoter for said gene formed and arranged for expression of said antibodies or cell mediated immunity elements in immunogenic non-pathogenic quantities; the promoter-gene sequence being introduced into a region of the viral genome which extends from the SmaI site close to the end of the inverted terminal repeat (ITR) up to the promoter for the early region 4(E4).

Preferably said canine adenovirus is a CAV-2 vaccine type strain of known long term safety modified so as to contain the inserted gene at a position close to the right hand terminus of the viral genome.

The inverted terminal repeat (ITR) is a DNA sequence found at both ends of the adenoviral genome. All adenoviruses examined to date have been shown to contain an ITR; however the lengths of these vary between serotypes. The ITR in CAV-2 is 197 base pairs (i.e., the region 0 to 197). The ITRs contain sequences which are essential for viral DNA replication and efficient packaging of the viral genomic DNA. However, we have identified a region at the end of the ITR of CAV-2 which can accommodate a substantial amount of extra DNA. This region extends from approximately the position of the Sma I site close to the end of the ITR (and just inside the ITR) up to the promoter for early region 4 (E4). Thus the Sma I site provides a convenient position into which foreign genes may be inserted. Other restriction sites may also be engineered into this region.

The SmaI site is a very convenient site at which to inset the gone, notwithstanding that it lies just inside the ITR. However, the insertion of material further into the ITR is unlikely to be successful as viral functions require the ITR's at the opposite ends of the virus to be able to line up together, which requires close sequence homology between the two ITR's.

The chosen non-pathogenic CAV-2 viral genome has been cloned into bacterial plasmids as a series of overlapping restriction fragments. A cloned fragment was required which spanned the Sma 1 site mentioned above and also included the right, and terminus of the virus. A clone carrying the 3.0 kb Sal 1 B fragment was therefore chosen.

Various genes may be inserted in the adenovirus DNA in accordance with the present invention to provide protection against a wide range of diseases and many such genes are already known in the art—the problem heretofore having been to provide a safe, convenient and effective vector for the genes.

Genes which may usefully be inserted include:
1) Gene(s) for the capsid proteins of canine parvovirus. There is in reality only one gene. However, differential splicing results in the production of two viral capsid proteins.
2) The genes for the capsid proteins of feline panleukopenia, which is a parvovirus very closely related to the canine parvovirus.
3) Genes (or segments) coding for the peplomeres of canine and feline coronavirus.
4) Genes for the hemagglutanin and capsid antigens of canine distemper virus.
5) The gene for the envelope glycoprotein of feline leukemia virus.
6) The gene for the envelope glycoprotein of rabies virus (various strains)
7) The gene for the envelope glycoprotein of feline immunodeficiency virus (FIV).

It is also possible that only fragments of genes may be used (where these are sufficient to generate an immunogenic protein or immunogenic cell response) rather than the complete sequence as found in the wild organism. Where available, synthetic genes may also be used. However, the present invention can be used with a wide variety of genes and is not limited to those set out above.

In some cases the gone for a particular antigen may contain a large number of introns or may be from an RNA virus, in these cases a DNA copy (cDNA) may be used.

In order for successful expression of the gone to occur, it must be inserted together with a suitable promoter sequence. Suitable promoter sequences for the genes mentioned above are known. The promoter is selected to give optimal expression of immunogenic protein or optimal cell mediated immunity according to known criteria.

The protein produced by expression in vivo in a recombinant virus-infected cell may be itself immunogenic. Moreover, the gone may produce more than one effective protein; or more than one foreign gene may be inserted in the viral genome.

Thus with the recombinant virus of the present invention, it is possible to provide protection in canivora against a wide variety of diseases.

In a second aspect the present invention provides a method of preparing a viable recombinant virus for producing antibodies or cell mediated immunity to an infectious organism in carnivora, which comprises inserting into a live non-parthogenic canine adenovirus the gene coding for the antigen which corresponds to said antibodies or induces said cell mediated immunity, together with an effective promoter therefore, to produce live non-pathogenic immunogenic recombinant adenoviruses.

Generally, the promoter-gene construct is cloned into a DNA sequence which is only a part of the entire viral genome. This sequence may be present in a plasmid which allows successful cloning to produce many copies of the sequence. The cloned sequence may then be included in the complete viral genome by the use of restriction enzymes corresponding to the restriction sites at each end of the sequence.

A third aspect of the invention relates to a plasmid containing such a viral DNA sequence containing a promoter-gene construct.

The DNA sequences of the virus and the construct may be identical to the native form or may be equivalent thereto in terms of the protein expressed. Moreover, the immunological protein (and hence the DNA) may have additions, deletions or substitutions immaterial to its immunological effect.

A fourth aspect of the invention provides a vaccine formulation which comprises the recombinant vaccine in association with an acceptable carrier. The vaccine may be formulated for a administration by oral dosage (e.g. as an enteric coated tablet), by injection or otherwise.

Embodiments of the invention will now be described by way of example only. Standard methods are as described in "Molecular Cloning—A Laboratory Manual", Second Edition, Sambrook, J., Fritsch, E. F., and Maniatis, T., Cold Spring Harbor Laboratory Press 1989.

EXAMPLE 1

In vitro Ligation

A gene of interest such as the rabies glycoprotein gene is first put under the control of a chosen promoter, (a number of different promoters are possible). The promoter-gone construct is then cloned into the Sma 1 size of the Sal 1 B fragment contained within a plasmid. This results in a plasmid which carries the right terminal 3.0 kb of CAV-2 with a chosen piece of DNA inserted just inside the boundary of the ITR.

Briefly, the modified right terminal section of the adenovirus genome is then incorporated into a complete viral genome as follows: Vital DNA is purified and cut with the restriction enzyme Sal 1, the cloned terminal Sal 1 fragment containing the promoter-gene construction is then released from the carrier plasmid and mixed with the cut viral DNA. The DNA fragments are then ligated back together.

A number of steps are taken to minimise the reformation of wild type genomes and to maximise the formation of the "correct" recombinant. For example the Sal I digested viral DNA can be run through a sucrose gradient in order to remove the right hand terminal Sal I fragment prior to ligation with the recombinant right hand terminal fragment.

The recombinant viral DNA is reintroduced to cultured dog cells using standard procedures in order to culture the virus. Individual viral plaques are picked and expanded in order that their genomic DNAs can be examined to confirm the presence of the recombinant gone.

Ligation products have been made by this method which incorporate the rabies gone, and the feline leukemia gone.

The DNA sequence of the right hand terminal region of the canine adenovirus type 2 genome is presented in FIG. 1 (SEQ ID NO: 1). The sequence is shown in the conventional 5' to 3' direction numbering from the righthand terminus. For clarity only the upper strand is shown. Various features are indicated: (1) the end of the inverted terminal repeat (ITR) at position 197; (2) the Sma I restriction enzyme cleavage site at position 180–185; (3) the TATA box of the E4 transcription unit at position 395–400.

EXAMPLE 2

Homologous Recombination

In Example 1 the target genes have been cloned into the SmaI site of the SalI B clone and subsequently the recombinant viruses were generated by in vitro ligation of viral DNA and plasmid fragments. In a variation of this method we have taken the recombinant SalI B clones (i.e. with the target genes inserted in the usual place) and extended them past the SalI site up to the third Kpn I from the right hand terminus (see FIG. 3 of N. Spibey and H. M. A. Cavanagh, J. Gen. Virol (1989), 70, 165–172). This was achieved by simply ligating the KpnI 8 fragment (which had been previously cloned into a standard bacterial cloning vector) into the appropriately cut recombinant SalI B plasmids. Because these recombinant right-hand terminal clones extend beyond the SalI site their incorporation into intact viral DNA was carried out via homologous recombination rather than by in vitro ligation.

The generation of recombinant viruses by homologous recombination is well established, briefly our methods are as follows: Viral DNA-protein complex was prepared from purified virions using standard protocols. A sample of the DNA protein complex was digested with the restriction enzyme SalI. A recombinant plasmid comprising the right terminal portion of the CAV-2 genome, extending from approximately 74 map units (the Kpn 1 site) up to the terminus (100 map units), with the chosen promoter-target gene construction inserted into the SmaI site near the ITR boundary, was taken and digested with a restriction enzyme such that plasmid was linearised but not cut within the CAV or target gene sequences. The two DNA samples (viral DNA protein complex and linearised plasmid) were then mixed in a molar ratio of 1:20 and transfected into a recipient cell line whose production is described hereafter.

EXAMPLE 3

Production of Ela Protein—Expressing Recipient Cell Line

Primary dog kidney cell cultures and established dog kidney cell cultures (MDCK cells) were taken and transfected with a mixture of two plasmids, (1) pGRIC, which comprises the left terminal EcoRI C fragment of CAV-2 cloned into the routine cloning vector bluescript. (2) pSV2-Neo, this plasmid contains the neomycin resistance gone under control of the Sv40 virus early promoter. The purpose of these transfections was to produce cell lines which constitutively produce the canine adenovirus Ela proteins (these proteins are encoded within the EcoRI C fragment, Spibey et al., Virus Research., 14, (1989) 241). We hypothesised that such a cell line would be more efficient at replicating transfected viral DNA because the E1 proteins are already present. The E1 proteins have a number of functions, however their major role can be regarded as regulatory i.e. they switch on other viral genes. Therefore if these proteins are already present then the transfected viral DNA may have a greater chance of being replicated and therefore avoid the cellular degradative processes. The plasmid conferring neumycin resistance was used as a co-selectable marker, i.e. individual clones of cells were selected on the basis of their neomycin resistance and then subsequently analysed for their production of CAV-2 Ela proteins. Transformed (i.e. Ela expressing) cell lines were obtained from both primary and established dog kidney cultures.

EXAMPLE 4

Transfection Method

All transfections were carried out as follows.

Day 1 Trypsinize cells and dilute them to a concentration of $1–1.5 \times 10^5$ cells per ml. The cells are then plated at $10^6$ cells per 100 mm dish (or the equivalent number per 175 $cm^2$ flask).

Day 2 Wash cells once in PBS. To each dish add 5 ml of serum free media containing 20 ug of DNA to be transfected and 50 ul of DEAE dextran (5 mg/ml stock). Ensure DNA/dextran solution is well mixed before adding to the cells.

After 4–6 hours remove DNA/dextran solution and add 5ml of serum free media containing 10% DMSO, leave for 1–2 min then remove and add complete media containing 0.1 mM chloroquine diphosphate. After 4 hours replace media with fresh complete media.

Incubate cells for required period of time. This can be up to 10 days to allow for a viral infection to spread throughout the whole culture.

Neomycin resistant clones were selected using standard protocols. Briefly, after transfection cells were allowed 24 hours in normal complete media before the addition of neomycin (800 ug/ml final concentration). The neomycin selection was continued for 7–10 days with media changed every 2 days. Resistant clones were identified, picked and expanded in neomycin free media for 3–4 days. A further round of dilution cloning in neomycin containing media was then carried out.

All cellular incubations were carried out at 37° C.

---

I claim:

1. A recombinant adenovirus for producing, in carnivora, antibodies or cell mediated immunity to an infectious organism selected from the group consisting of feline leukaemia virus, rabies virus, and feline immunodeficiency virus, which comprises a live non-pathogenic immunogenic viable canine adenovirus which is canine adenovirus 2 (CAV-2) modified so as to contain a gene coding for an antigen which induces said antibodies or induces said cell mediated immunity, in association with an effective promoter for said gene formed and arranged for expression of said antigen in immunogenic non-pathogenic quantities; said gene selected from the group consisting of the envelope glycoprotein gene of feline leukaemia virus, the envelope glycoprotein gene of rabies virus, and the envelope glycoprotein gene of feline immunodeficiency virus; the promoter-gene sequence introduced into a region of the CAV-2 inverted terminal repeat (ITR) at the 3' end of the viral genome, said region extending from the SmaI site closest to the end of the inverted terminal repeat (ITR) to the 3' end of the ITR.

2. A recombinant adenovirus according to claim 1 wherein the promoter-gene sequence is introduced into the SmaI site.

3. A host cell containing a recombinant adenovirus according to claim 1 and capable of expressing the gene encoded by said promoter-gene sequence, said host cell transformed with a sequence encoding and expressing canine adenovirus Ela proteins.

4. A method of preparing a recombinant adenovirus for producing antibodies or, cell mediated immunity, in carnivora, to an infectious organism selected from the group consisting of feline leukaemia virus, rabies virus, and feline immunodeficiency virus which comprises modifying a live non-pathogenic immunogenic viable canine adenovirus which is canine adenovirus 2 (CAV 2) so as to contain a gene coding for an antigen which induces said antibodies or induces said cell mediated immunity, in association with an effective promoter for said gene formed and arranged for expression of said antigen in immunogenic non-pathogenic quantities; said gene selected from the group consisting of gene for the envelope glycoprotein, of feline leukaemia virus, gene for the envelope glycoprotein of rabies virus, and gene for the envelope glycoprotein of feline immunodeficiency virus; the promoter-gene sequence introduced into a region of the CAV-2 inverted terminal repeat (ITR) at the 3' end of the viral genome, said region extending from the SmaI site closest to the end of the inverted terminal repeat (ITR) to the 3' end of the ITR.

5. A method according to claim 4 wherein the recombinant virus is replicated by transfection into a cell line expressing canine adenovirus Ela proteins.

6. A plasmid which contains a live non-pathogenic immunogenic viable canine adenovirus 2 (CAV-2) inverted terminal repeat DNA sequence from the region extending from the SmaI site closest to the end of the inverted terminal repeat (ITR) at the 3' end of the CAV-2 genome to the 3' of said inverted terminal repeat, said CAV-2 DNA sequence modified by the introduction of a promoter-gene sequence wherein the gene is selected from the group consisting of feline leukemia virus envelope glycoprotein gene, rabies virus envelope glycoprotein gene, and feline immunodeficiency virus envelope glycoprotein gene.

7. A vaccine formulation which comprises the recombinant adenovirus according to claim 1 together with an acceptable carrier therefor.

8. A recombinant viral expression vector which can express an inserted heterologous gene, said vector comprising:

(a) a non-pathogenic viable canine adenovirus 2 (CAV-2) genome; and (b) a heterologous gene inserted into a region of the CAV-2 inverted terminal repeat at the 3' end of the viral genome, said region extending from the SmaI site closest to the end of the inverted terminal repeat (ITR) to the 3' end of the inverted terminal repeat, said heterologous gene in association with an effective promoter for said gene.

9. The viral expression vector of claim 8, wherein said heterologous gene is selected from the group consisting of feline leukaemia virus envelope glycoprotein gene, rabies virus envelope glycoprotein gene, and feline immunodeficiency virus envelope glycoprotein gene.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 652 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CATCATCAAT  AATATACAGG  ACAAAGAGGT  GTGGCTTAAA  TTTGGGCGTT  GCAAGGGGCG        60

GGGTCATGGG  ACGGTCAGGT  TCAGGTCACG  CCCTGGTCAG  GGTGTTCCCA  CGGGAATGTC       120
```

| | | | | | | |
|---|---|---|---|---|---|---|
| CAGTGACGTC | AAAGGCGTGG | TTTTACGACA | GGGCGAGTTC | CGCGGACTTT | TGGCCGGCGC | 180 |
| CCGGGTTTTT | GGGCGTTGTG | CCTATTTGTG | GTTTGTGGT | TGACAGGGTG | ACAAGGACGT | 240 |
| GCTGTACTTT | TTGTGAACTT | TCCGGGCCAA | CCGCCAAAGG | GAAACTGCAC | TTAACATTTA | 300 |
| CCACGCGCCC | ACAATTTATG | ACTGTACTTG | GCACCACTTC | CTCAAACGCC | CCGTTATATT | 360 |
| CCTTTTGCTT | TTCCACACGC | CCTACTTTGA | GGACTATATA | AACGCTGTGC | TTGGCATTTC | 420 |
| ATCCTCATAG | CTCTCCTCTG | ACAGCCAGCC | GTCCGTGAGT | ACTATGGCAG | CTTTAGGAGT | 480 |
| GTCTATGGGA | GCATGTTTTT | GTCTGAGGCT | TCACAAGAGT | CTAGTGGAGA | GTGTGTGTGC | 540 |
| TCAACTGAGA | CTTACGAACT | TTTTGCCTTC | TGAACTCGCC | GTGTGGTGTT | TAGCCTTATT | 600 |
| AGGGCCCAGG | AAGTGCGTCC | GTGTCCTACC | TTGCCGCGGC | TGTTTCGGTT | TA | 652 |